United States Patent [19]
Potter

[11] 4,202,203
[45] May 13, 1980

[54] OSCILLATOR DETECTOR

[76] Inventor: Bronson M. Potter, R.F.D. 1, Mason, N.H. 03048

[21] Appl. No.: 972,651

[22] Filed: Dec. 26, 1978

Related U.S. Application Data

[63] Continuation-in-part of Ser. No. 827,130, Aug. 24, 1977, abandoned.

[51] Int. Cl.² ............................................. G01N 27/18
[52] U.S. Cl. ................................................. 73/61.1 R
[58] Field of Search ...................... 73/53, 61.1 R, 204, 73/295

[56] References Cited

U.S. PATENT DOCUMENTS

| | | | |
|---|---|---|---|
| 3,181,557 | 5/1965 | Lannan, Jr. ...................... | 73/295 X |
| 3,548,637 | 12/1970 | Wicks ........................................ | 73/53 |
| 3,906,391 | 9/1975 | Murdock ................................ | 331/66 |

*Primary Examiner*—Gerald Goldberg
*Assistant Examiner*—Joseph W. Roskos

[57] ABSTRACT

An alien liquid detector employs a monitoring element and an oscillatory electronic circuit for maintaining the temperature of the monitoring element substantially above ambient temperature. The output wave form, e.g., frequency of oscillation or wave shape, of the oscillatory circuit depends upon the temperature-dependent electrical characteristic of the monitoring element. A predetermined change in the output waveform allows water to be discriminated from another liquid, e.g., oil. Features of the invention employing two thermistors in two oscillatory circuits include positioning one thermistor for contact with water and the other thermistor above the oil-water interface to detect a layer of oil if present. Unique oscillatory circuit arrangements are shown that achieve effective thermistor action with an economy of parts and energizing power. These include an operational amplifier employed in an astable multivibrator circuit, a discrete transistor-powered tank circuit, and use of an integrated circuit chip.

14 Claims, 6 Drawing Figures

OSCILLATOR DETECTOR

This is a continuation-in-part of application Ser. No. 827,130 filed Aug. 24, 1977, now abandoned.

This invention relates to devices for sensing the presence of an alien immiscible liquid for purposes such as detecting oil spills on water.

The purpose of the invention is to provide detection devices that are simple, durable, sensitive and can be made at low cost. Another object is to enable liquids that are difficult to discriminate from water, for example, to be reliably detected.

According to the invention, the device which accomplishes these objects comprises a monitoring element exposed for heat transfer contact with an alien immiscible liquid when present on a desired liquid, the monitoring element having an electrical characteristic that changes as a single-valued function of temperature, e.g., a thermistor (a device responsive to change its effective electrical resistance in correspondence with temperature change). The monitoring element is connected in and energized by an oscillatory electronic circuit, the oscillatory electronic circuit being arranged to heat the monitoring element to a temperature substantially above the temperature of the desired liquid, the amount of heat conducted away from the monitoring element and thereby the instant level of temperature of the monitoring element above the temperature of the liquid being dependent upon the thermal absorptive properties of the liquid, the oscillation waveform of said oscillatory circuit being dependent upon the temperature-dependent electrical characteristic of the monitoring element. Means are provided to derive an output signal from the oscillating circuit dependent upon this waveform. Because the resistance of a thermistor is a single-valued function of its temperature, the waveform dependent output signal is thus a measure of the thermal loss of the monitoring element. An indicator responsive to a predetermined change in the oscillator waveform indicates the presence of the alien liquid. As a detector, therefore, a device embodying the invention allows one surrounding medium to be distinguished from another as in the detection of oil floating on water.

While thermistors per se have been used to respond, e.g., to oil, see Bock & Eckert in "Detection of Oil in Sewers," IEEE Transactions on Geoscience Electronics, Volume GE-10, April, 1972, and Elliot et al., U.S. Pat. No. 2,972,684, or to other liquid interfaces, see Lannan U.S. Pat. No. 3,181,557, such prior art do not give benefits obtainable with the present invention. By having a thermistor or other suitable monitoring element connected in circuit in such manner that it is heated above the temperature of the surrounding liquid, it is possible to discriminate between two different surrounding liquids, e.g., oil and water, despite both being at the same actual temperature.

In a preferred embodiment of the invention, an operational amplifier is connected as a modification of the well known astable multivibrator in which a temperature dependent thermistor is substituted for a temperature independent resistor. In the positive feedback path, the output of the operational amplifier is connected to ground through a series connection of a thermistor and a reference resistor comprising a voltage divider. The midpoint of this divider is connected to the non-inverting input to the operational amplifier providing positive feedback regeneration with all of the feedback current in the positive feedback path, flowing through the thermistor. The output of the operational amplifier is also connected to ground through the series connection of a resistance and capacitance comprising another divider. The midpoint of this divider is connected to the inverting input to the operational amplifier. Because of the positive feedback, output voltage of the operational amplifier oscillates between saturation at plus and minus the supply voltage, generating a square wave. The output saturates at the positive supply voltage whenever the difference between the non-inverting and inverting inputs is a positive value. When it is a negative value, the output saturates in the negative direction. Thus the output is either plus or minus the supply voltage, so power continually flows through the thermistor and reference resistor to ground. This power flow heats the thermistor to a temperature substantially above the temperature of the liquid in which it is disposed, e.g. the desired liquid, and temperature and resistance response will stabilize. It is well known that the frequency of oscillation of such a multivibrator depends on the resistance in the positive feedback path, and hence, in this case, on the thermistor resistance. Therefore, if the thermistor is in an alien liquid, the thermistor temperature and resistance response will stabilize about a new level, altering the frequency of oscillation. A predetermined change in frequency indicates the presence of the alien immiscible liquid, allowing, for example, oil to be discriminated from water.

In another preferred embodiment, the oscillatory circuit heats the thermistor to a circuit flip temperature substantially above ambient at which point the power flow through the thermistor is reduced allowing the thermistor to cool for a time which depends on the overall circuit arrangement. Power is then reapplied to the thermistor, again heating it toward the flip temperature. The time required to heat the thermistor to the flip temperature depends on whether the thermistor is immersed in an alien liquid, and hence the overall oscillation frequency of the circuit indicates the presence or absence of an alien liquid. Such an embodiment is realized with an emitter-coupled multivibrator in which a first transistor means supplies heating power to the thermistor and a second transistor means, connected in a positive feedback relationship to the first transistor means, causes the power flow through the thermistor to oscillate. The frequency of oscillation depends on the presence or absence of an alien liquid.

In another embodiment, an integrated circuit means, arranged to oscillate, supplies heating power to the thermistor. Again, the frequency of oscillation depends on the presence or absence of an alien liquid.

In another embodiment, an operational amplifier is connected in a positive feedback Wien-bridge, oscillatory circuit. A thermistor, located in the negative feedback path, is selected so that, for example, the output signal is a sine wave when the thermistor is exposed to detect air. The output waveform distorts from a pure sine wave toward a square wave as heat transfer from thermistor to a surrounding medium increases as when the detector element is exposed to oil or water, allowing one surrounding medium to be discriminated from another. The invention of course requires that the thermistor be exposed as a detector element, e.g., submerged in fluid to be sensed, which of course distinguishes the invention from the known use of a thermistor in a Wien-bridge circuit as a stabilizing element for the circuit.

A further embodiment of the invention is a detector comprising an oscillatory circuit described above and a reference, including a means for producing a signal representing the difference between the output signal of the oscillatory circuit and the reference. In one embodiment, the reference comprises a second oscillatory circuit, one thermistor being exposed to a reference fluid and the other thermistor to a fluid at the same temperature as the reference fluid, whose heat absorptive conditions, e.g., specific heat, may vary from those of the reference fluid. Means are provided to produce a signal representing the difference between the output signals of the two oscillatory circuits. When this embodiment is employed as an oil detector, the reference thermistor is exposed to water and the thermistor of the other circuit is exposed to fluid which may be oil or water. A difference output thus indicates the presence of oil.

The embodiments and features of the invention herein will be further understood in conjunction with the following drawings in which.

DESCRIPTION OF THE PREFERRED EMBODIMENTS

Figure 1:
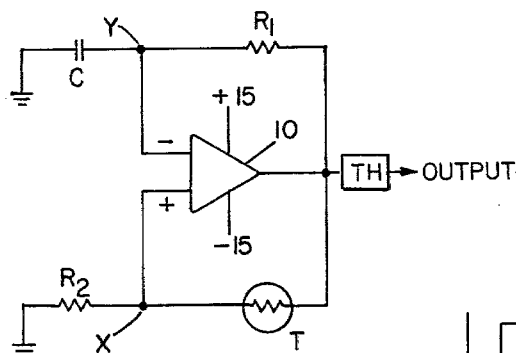
FIG. 1 is a schematic diagram of an embodiment of the invention employing an operational amplifier.

Referring to FIG. 1, an LM358 operational amplifier 10 is connected in an astable multivibrator circuit. In the positive feedback path, the operational amplifier 10 output is connected to ground through thermistor T, Fenwal GB38L1, and 1330 $\Omega$ resistor $R_2$. The midpoint X of the $R_2$-T connection is connected to the non-inverting input to operational amplifier 10. Another path from the output of operational amplifier 10 to ground is connected through 50K resistor $R_1$ and 680 pf capacitor C. The midpoint of the $R_1$-C connection is connected to the inverting input to operational amplifier 10. When the circuit is turned on the output is at the supply voltage of +15 volts and the $R_2$-T junction is at $\beta$ times 15 volts where $\beta = R_2/(R_2+T)$ and T is the thermistor resistance at turn on. The voltage across capacitor C begins charging toward +15 volts. When this voltage exceeds $\beta$ times 15, the net input to operational amplifier 10 becomes negative since the lead from the $R_1$-C junction Y is connected to the inverting input. The output snaps rapidly from positive to negative saturation. Capacitor C then begins charging toward $-15$ volts, and when it exceeds $\beta$ times 15 volts, the output quickly saturates at +15 volts. This process continues, producing a square wave at the output of operational amplifier 10. As the circuit oscillates, power is continually flowing through thermistor T, causing it to heat to a temperature substantially above ambient. This frequency of oscillation is given by the expression $$f = \frac{1}{2R_1C \log_e \frac{(1+\beta)}{(1-\beta)}}.$$

If the liquid in which thermistor T is disposed changes, the temperature, and hence resistance, of thermistor T changes, altering the frequency of oscillation. A threshold circuit TH monitors the output voltage and produces an output when a predetermined change in the voltage V is sensed to indicate the presence of an alien liquid.

Figure 1A:
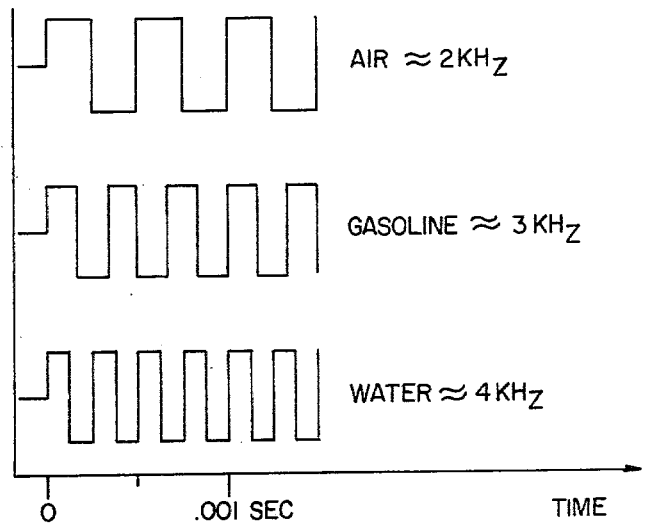
FIG. 1a shows representative outputs of the circuit of FIG. 1 when the thermistor is exposed to different media.

FIG. 1a displays representative output signal waveforms of the circuit of FIG. 1 when thermistor T is exposed to the different surrounding media of air, gasoline and water.

Figure 2:
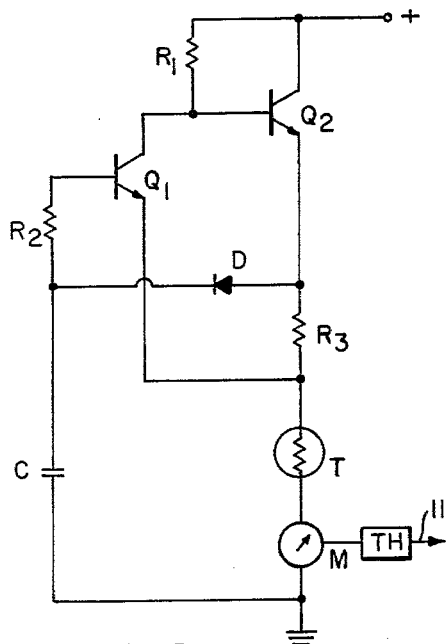
FIG. 2 is a schematic diagram of an embodiment of the invention employing an emitter coupled multivibrator.

Referring to FIG. 2, transistors $Q_1$ and $Q_2$ are connected in an emitter-coupled multivibrator arrangement. At turn-on transistor $Q_2$ will conduct, near saturation, because of heavy base bias allowing current to flow through the $Q_2$ emitter, 560 $\Omega$ resistor R3, thermistor T and frequency meter M to ground. As thermistor T warms, flow increases through R3 until the IR voltage overcomes the forward voltage of diode D so that the base of $Q_1$ is biased on. The collector of $Q_1$ deprives $Q_2$ of base bias current, reducing flow through the emitter circuit of $Q_2$. $Q_1$'s emitter sees the reduced IR drop in resistance in the emitter circuit of $Q_2$ as a forward current sustained by the charge stored in 10 $\mu$f capacitor C. $Q_1$ then flips $Q_2$ off until C discharges, at which time $Q_1$ turns off and the emitter circuit of $Q_2$ begins to conduct, starting the cycle again.

Figure 3:
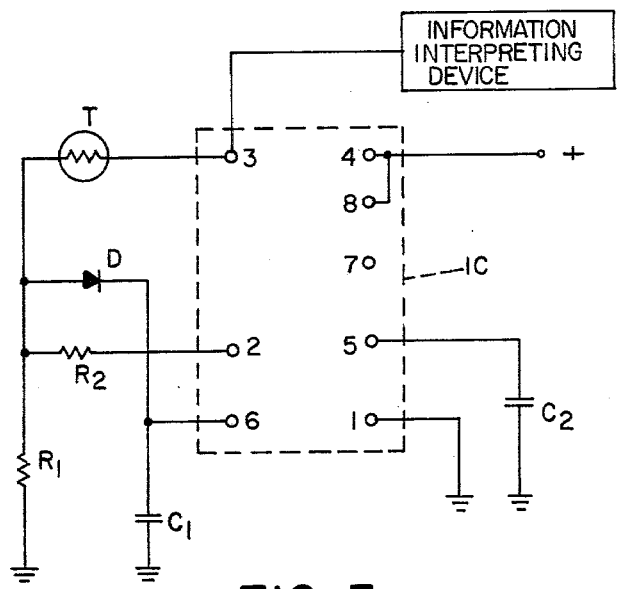
FIG. 3 is a schematic diagram of an embodiment of the invention employing an integrated circuit.
Figure 4:
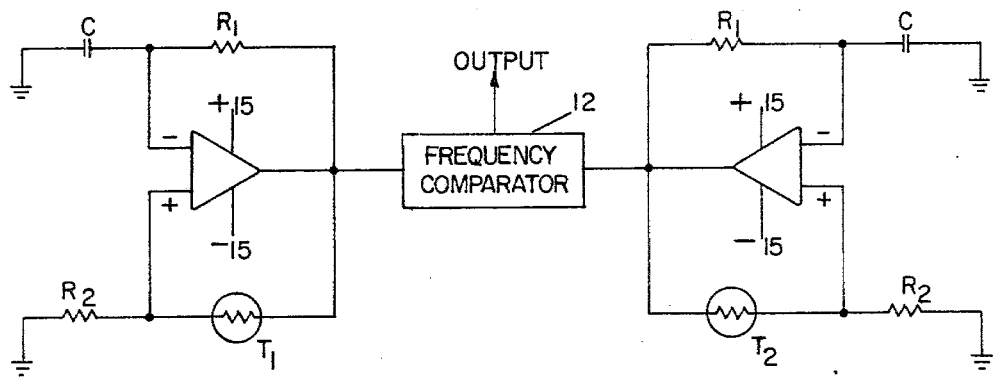
FIG. 4 is a schematic diagram of circuitry combining two of the oscillatory circuits of FIG. 1.

The time required to heat the thermistor to flip temperature depends on the fluid in which the thermistor is disposed. Since the heat-up time of the thermistor changes with changes in the heat absorptive properties of that fluid, repetition rate, the frequency of the waveform, changes in the presence of an alien liquid. Meter M measures this frequency of oscillation and threshold circuit TH produces an output over line 11 to indicate the presence of an alien liquid. The frequency of oscillation is approximately 1 Hz in water, and uses approximately 15 Mw of power. Referring to FIG. 3, thermistor T is connected to an integrated circuit IC 555, arranged to oscillate at a frequency dependent upon the resistance of thermistor T. When the circuit is turned on, output terminal 3 is at positive battery potential because control terminals 2 and 6 are held at a negative potential by 0.27 $\mu$f capacitor $C_1$. Current therefore flows through thermistor T and 560 $\Omega$ resistor $R_1$, to ground, heating thermistor T. As T warms, the voltage at terminals 2 and 6 rises until it reaches ⅔ of the battery potential. The time required for this voltage rise depends on the resistance of T and thus on the heat absorptive characteristics of the surrounding medium. Integrated circuit IC is designed to flip at this voltage, turning terminal 3 to ground potential. Current stops flowing through T allowing it to cool. Capacitor $C_1$ discharges slowly through 10 m $\Omega$ resistor $R_2$ until the voltage across it reaches ⅓ of the battery potential. At this point, integrated circuit IC flips on again, returning terminal 3 to positive battery potential. The oscillation continues in this manner, its waveform frequency an indication of the heat absorptive properties of the medium to which thermistor T is exposed. Referring to FIG. 4, the outputs of two of the multivibrator circuits of FIG. 1 are compared in frequency comparator 12. The output of comparator 12 is thus the difference in the frequency of oscillation of the multivibrator circuits having thermistors $T_1$ and $T_2$ as elements. One of the circuits acts as a reference. Whenever thermistors $T_1$ and $T_2$ are exposed to surrounding media having difference heat absorptive properties, the frequencies of oscillation of the two multivibrator circuits will differ giving rise to an output from frequency comparator 12. If, for example, thermistor $T_2$, the reference, is exposed for contact with water and $T_1$ is exposed for contact with an oil layer which may be present on the surface of the water, the frequencies of oscillation of the two circuits will differ because water conducts heat away from $T_2$ at a greater rate than the oil conducts heat away from sensing thermistor $T_1$ assuming that oil and water are at the same temperature.

Figure 5:
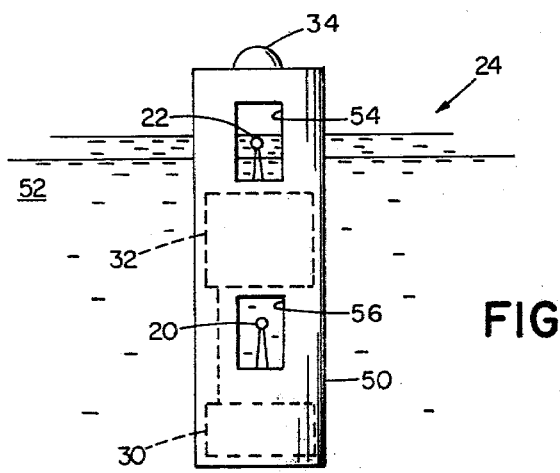
FIG. 5 is a diagrammatic view of an oil detector employing the circuit of FIG. 4.

FIG. 5 shows the invention embodied as an oil detection unit employing the circuit of FIG. 4. The oil detection system includes a buoyant, tubular housing 50 designed to float on water 52 to be monitored. Housing 50 has upper and lower recesses 54, 56. The buoyancy of housing 50 is such that recess 54 is disposed at the surface of the water and recess 56 is submerged. Reference thermistor 20 is disposed in recess 56 so that it remains under water. Monitoring thermistor 22 is disposed in recess 54 at the air-liquid interface so that it is exposed to oil should a film of oil 24 exist on the monitored surface. The oil detection unit may be self-contained and include batteries 30 (which function as ballast), the electronic circuit of FIG. 4, 32, and an output indicator 34 on its upper surface. In another embodiment, the unit may be connected by flexible cable (not shown) to a remote power supply and to remote output indicator circuitry.

While the preferred devices used to perform the thermistor functions of this invention are those semiconductor units sold as "thermistors", it will be understood that certain of the advantages of the invention can be obtained using other devices, or combinations whose effects upon the circuit varies with temperature in single-valued relation. For instance, a temperature-sensitive diode may be employed in certain instances, provided its temperature characteristic corresponds to the needs of the particular application involved.

What is claimed is:

1. A detector for detecting an alien immiscible liquid in the presence of a desired liquid, e.g., for detecting oil pollution at a surface boundary of water, comprising a monitoring element exposed for heat transfer contact with said alien liquid when present, said monitoring element having an electrical characteristic that changes as a single-valued function of temperature, said monitoring element connected in and energized by an oscillatory electronic circuit, said oscillatory electronic circuit being arranged to heat said monitoring element to a temperature substantially above ambient temperature, the amount of heat conducted away from said monitoring element and thereby the instant level of temperature of the monitoring element above the temperature of the liquid being dependent upon the thermal absorptive properties of said liquid, the oscillation waveform of said oscillatory circuit being dependent upon the temperature-dependent electrical characteristic of said monitoring element, means to derive an output signal from said circuit dependent upon said waveform and indicating the thermal loss of said monitoring element to said surrounding liquid, and an alien liquid indicator circuit responsive to a predetermined change in said oscillation waveform for indicating the presence of said alien liquid, said predetermined change related to the difference in the specific heats of the alien and the desired liquids.

2. The detector of claim 1 wherein said monitoring element is a thermistor.

3. The detector of claim 2 wherein said oscillatory circuit comprises operational amplifier means connected as an astable multivibrator, the frequency of said oscillation dependent upon the resistance of said thermistor, said thermistor being connected in a positive feedback path between the output of said operational amplifier and the non-inverting input of said operational amplifier such that all of the feedback current in said positive feedback path flows through said thermistor.

4. The detector according to claim 2 wherein said oscillatory circuit is constructed (a) to be in a first power flow condition to heat said thermistor to a flip temperature, (b) to respond to the resistance of said thermistor corresponding to said flip temperature to cause change to a second power flow condition to allow said thermistor to cool, (c) to maintain said reduced power flow condition for a time dependent upon said circuit and to reapply said first power condition to reheat said thermistor toward said flip temperature, the time segment until the next flip being dependent upon the heat absorptive characteristics of said surrounding liquid.

5. The detector of claim 4 wherein said oscillatory electronic circuit comprises an emitter coupled multivibrator including a first transistor means for supplying heating power to said thermistor and second transistor means connected in a positive feedback relationship to said first transistor means causing said heating power flow through said thermistor to be oscillatory, said frequency of oscillation dependent upon said heat absorptive characteristics of said surrounding liquid.

6. The detector of claim 4 wherein said oscillatory circuit comprises integrated circuit means arranged to oscillate, said frequency of oscillation dependent upon said heat absorptive characteristics of said surrounding liquid.

7. The detector of claim 6 incorporated into a probe for positioning said thermistor at the surface of liquid that may be contaminated.

8. The detector of claim 1 and further including a reference, and means for producing a signal representing the difference between the output signal of said oscillatory circuit and said reference.

9. The detector of claim 8 wherein said reference comprises a second monitoring element and a second oscillatory circuit, said second oscillatory electronic circuit being arranged to heat said second monitoring element to a temperature substantially above ambient temperature, the oscillation waveform of said second oscillatory circuit being dependent upon the temperature-dependent electrical characteristic of said second monitoring element, one of said monitoring elements being exposed to said desired liquid and the other monitoring element being disposed for exposure to said alien liquid if present, and means to produce a signal representing the difference between the output signals of said two oscillatory circuits.

10. An oil detector comprising the detector of claim 9 wherein said one monitoring element is exposed to water and said other monitoring element is exposed to a liquid which may be oil or water.

11. The detector of claim 1 characterized in that said monitoring element is incorporated in a probe for positioning said monitoring element at the surface of said desired liquid.

12. The detector of claim 11 wherein said probe comprises a float adapted to freely float upon the surface of said liquid.

13. The detector of claim 1 wherein said oscillatory circuit comprises operational amplifier means and a voltage divider network consisting of said monitoring element and a resistor, said resistor having a resistance value of the same order of magnitude as said monitoring element at ambient temperature, said monitoring element being connected in a positive feedback path from the output of said operational amplifier and the junction between said monitoring element and said resistor being connected to an input of said operational amplifier.

14. The detector of claims 1, 2, 10, 12 or 13 wherein said alien fluid to be sensed is floating on water, characterized in that said monitoring element has an electrical resistance decreasing with increasing temperature, whereby the heating effect of said monitoring element, when said floating liquid has lower viscosity than water, is less than when water is present, thereby enabling reduced convection losses in the presence of high oil distillates and the like to enable detection thereof.

* * * * *